US010299984B2

(12) United States Patent
Amblard et al.

(10) Patent No.: US 10,299,984 B2
(45) Date of Patent: May 28, 2019

(54) SYSTEM FOR RESPIRATORY DISORDER THERAPY WITH STABILIZATION CONTROL OF STIMULATION

(71) Applicants: SORIN CRM SAS, Clamart (FR); INSERM-INSTITUT DE LA RECHERCHE MÉDICALE, Paris (FR); UNIVERSITÉ JOSEPH FOURIER, Grenoble (FR); UNIVERSITÉ DE RENNES 1, Rennes (FR)

(72) Inventors: Amel Amblard, Sceaux (FR); Laurence Graindorge, Thouaré sur Loire (FR); Delphine Feuerstein, Issy les Moulineaux (FR); Alfredo Hernandez, Cesson Sévigné (FR); Jean-Louis Pépin, Grenoble (FR)

(73) Assignees: SORIN CRM SAS, Clamart (FR); INSERM-INSTITUT DE LA RECHERCHE MÉDICALE, Paris (FR); UNIVERSITÉ JOSEPH FOURIER, Grenoble (FR); UNIVERSITÉ DE RENNES 1, Rennes (FR)

( * ) Notice: Subject to any disclaimer, the term of this patent is extended or adjusted under 35 U.S.C. 154(b) by 585 days.

(21) Appl. No.: 14/961,379

(22) Filed: Dec. 7, 2015

(65) Prior Publication Data

US 2016/0158092 A1    Jun. 9, 2016

(30) Foreign Application Priority Data

Dec. 8, 2014   (FR) ...................................... 14 62041

(51) Int. Cl.
*A61H 23/00* (2006.01)
*A61B 5/00* (2006.01)
(Continued)

(52) U.S. Cl.
CPC ......... *A61H 23/004* (2013.01); *A61B 5/0205* (2013.01); *A61B 5/0826* (2013.01);
(Continued)

(58) Field of Classification Search
CPC ................. A61H 23/004; A61H 23/02; A61H 2230/405; A61H 2230/207;
(Continued)

(56) References Cited

U.S. PATENT DOCUMENTS 4,788,968 A * 12/1988 Rudashevsky ..... A61H 23/0218
310/30
5,277,694 A * 1/1994 Leysieffer ................. A61F 2/18
181/130
(Continued)

FOREIGN PATENT DOCUMENTS

EP    1 317 943 A1    6/2003
EP    1 319 421       6/2003
(Continued)

OTHER PUBLICATIONS

U.S. Appl. No. 14/961,348, filed Dec. 7, 2015, Amblard et al.
(Continued)

*Primary Examiner* — Steven O Douglas
(74) *Attorney, Agent, or Firm* — Foley & Lardner LLP

(57) ABSTRACT

A system includes a processor configured to generate stimulation control signals in response to a detection of a respiratory disorder. The system further includes at least one kinesthetic effector with a vibrating electromechanical transducer applied to a site on a patient's skin for delivering a kinesthetic stimulation energy determined by the control signals. The processor is further configured to determine the effectiveness of a stimulation by detecting a cessation of the respiratory disorder. The processor is further configured to
(Continued)

extend the stimulation control signals for a determined duration following the cessation of the respiratory disorder.

10 Claims, 4 Drawing Sheets

(51) Int. Cl.
    *A61N 1/36*     (2006.01)
    *A61B 5/0205*     (2006.01)
    *A61B 5/08*     (2006.01)
    *A61H 23/02*     (2006.01)
    *A61B 5/0402*     (2006.01)

(52) U.S. Cl.
    CPC .......... *A61B 5/4818* (2013.01); *A61B 5/4836* (2013.01); *A61H 23/02* (2013.01); *A61N 1/3611* (2013.01); *A61B 5/0402* (2013.01); *A61H 2201/10* (2013.01); *A61H 2201/5007* (2013.01); *A61H 2201/5012* (2013.01); *A61H 2205/027* (2013.01)

(58) Field of Classification Search
    CPC ...... A61H 2230/065; A61H 2201/5058; A61H 2201/5015; A61H 39/002; A61H 2201/0157; A61H 2203/0456; A61H 2205/027; A61H 2230/04; A61H 2230/045; A61B 5/4818; A61N 1/3611
    See application file for complete search history.

(56) References Cited

U.S. PATENT DOCUMENTS

| | | |
|---|---|---|
| 5,555,891 A | 9/1996 | Eisenfeld |
| 2007/0032733 A1 | 2/2007 | Burton |
| 2007/0208269 A1* | 9/2007 | Mumford ............ A61B 5/0002 600/546 |
| 2008/0009915 A1 | 1/2008 | Moses et al. |
| 2008/0033304 A1* | 2/2008 | Dalai ................... A61B 5/0205 600/484 |
| 2008/0154330 A1 | 6/2008 | Tehrani et al. |
| 2009/0192556 A1* | 7/2009 | Wu ...................... A61B 5/0031 607/3 |
| 2010/0048985 A1 | 2/2010 | Henke et al. |
| 2010/0087701 A1* | 4/2010 | Berka .................. A61M 21/02 600/27 |
| 2012/0089199 A1* | 4/2012 | Bolea .................. A61N 1/0556 607/42 |
| 2013/0144152 A1 | 6/2013 | Cervantes |
| 2014/0051938 A1 | 2/2014 | Goldstein et al. |
| 2014/0088378 A1 | 3/2014 | Muzet |

FOREIGN PATENT DOCUMENTS

| | | |
|---|---|---|
| EP | 2 313 151 | 4/2011 |
| WO | WO-96/28093 | 9/1996 |
| WO | WO-2007/141345 | 12/2007 |
| WO | WO-2009/154458 | 12/2009 |

OTHER PUBLICATIONS

U.S. Appl. No. 14/961,403, filed Dec. 7, 2015, Amblard et al.
Preliminary Search Report for French Patent Application No. 1462039, dated Jul. 28, 2015, 2 pages.
Preliminary Search Report for French Patent Application No. 1462041, dated Jul. 28, 2015, 2 pages.
Preliminary Search Report for French Patent Application No. 1462054, dated Apr. 8, 2015, 2 pages.

* cited by examiner

SYSTEM FOR RESPIRATORY DISORDER THERAPY WITH STABILIZATION CONTROL OF STIMULATION

CROSS-REFERENCE TO RELATED PATENT APPLICATIONS

This application claims the benefit of and priority to French Patent Application No. 1462041, filed Dec. 8, 2014, which is incorporated herein by reference in its entirety.

BACKGROUND

The present disclosure relates to the diagnosis and therapy of sleep disorders.

More particularly, the disclosure relates to a "kinesthetic stimulation" device which is a device for external sensory stimulation of the patient by a vibrator in contact with the skin in a sensitive and precise region of the body of the patient. Activating this vibrator has the effect of locally exciting cutaneous or mechanoreceptor endings of the skin, and triggering a response from the patient's autonomic nervous system, with sympathetic predominance (hereinafter "autonomic response").

The autonomic response to sympathetic activation is observable on the major modulator effects of cardiac activity, for example a chronotropic effect (e.g., a heart rate increase, a decrease in RR intervals, etc.) and an inotropic effect (e.g., heart contractility increase, etc.). This autonomic response is also observable on the peripheral vasoconstriction, which is increased during sympathetic autonomic activation. In addition to these effects on cardiac activity, a sympathetic activation causes responses in the respiratory system and/or in the central nervous system (autonomic awakenings).

This is a noninvasive method for acting on a number of sleep disorders in alternative ways to the conventional therapeutic approaches that are based on the application of a continuous positive airway pressure through a face mask (a therapy by CPAP), the use of a mandibular orthosis, and/or electrical stimulation of the hypoglossal nerve, which involves the implantation of a pacemaker.

In particular, the respiratory disease known as "sleep apnea syndrome" (SAS) is characterized by the frequent occurrence (at least 10 to 20 times per hour) of apneas during a patient's sleep phase, an "apnea" (or respiratory pause) being defined as a temporary cessation of breathing for a duration longer than 10 s. SAS can also be characterized by the occurrence of hypopnea under the same conditions, a "hypopnea" being defined as a significant decrease (without interruption) of the breathing rate, typically a decrease of more than 50% compared to a previous reference average value.

This pathology reaches more than 4% of the population and more than 50% of patients with heart failure. To protect the individual against asphyxiation due to the decrease in blood oxygen concentration during the interruption or the reduction of respiratory rate, the body adapts itself but with a deleterious effect on sleep, causing unconscious micro-arousals. The consequence is daytime sleepiness when in a wakeful stage, with loss of attention and increased risk of accident. Furthermore, several studies have shown a higher incidence of blood disorders in patients with SAS such as hypertension, ventricular arrhythmias, myocardial infarction and heart failure.

Several documents describe the ability to stop apnea episodes through a stimulation therapy. For example, U.S. Pat. No. 5,555,891 A describes a vibrotactile stimulation system to stop apnea in newborns. The objective is to provide a system capable of detecting apnea and of stimulating the child to stop apnea, with a stimulation energy that may vary to avoid habituation. The applied energy is important and often involves arousal.

WO2007141345 A1 describes a remote monitoring system for neonatal units, to detect and stimulate infant apnea-bradycardia. This application refers to an adjustment of the stimulation energy based on the measured heart rate of the infant. In the proposed method, no analysis of respiratory signals is performed. This prevents the differentiation of types of detected or expected sleep disorders, and therefore, the adjustment of stimulation strategies based on said type of disorder. Moreover, this approach limits the delivery of therapy to the time interval during which the disorder is present.

WO 96/28093 A1 also teaches a system that delivers a stimulus to reduce the frequency or duration of an apnea episode. At the stimulation level, this document simply describes the low and high limits of the stimulation energy that may stop apnea without waking the patient.

US 2008/009915 A1 discloses a system that detects respiratory disorders using a nasal or other cannula and applies a particular vibratory stimulation in the ear region. The objective is to stop apnea, without waking the patient, by stimulation which may be manually or automatically adjusted, depending on physiological characteristics of the patient or of the sleep cycles. This document also generally cites the optimization of the stimulation parameters to fit the severity of the patient's disorder, without giving details on the stimulation parameters adjustment. A change in parameters to prevent habituation is also cited.

US 2010/0048985 A1 describes a similar device for applying stimuli by various natures (e.g., audio or ultrasonic stimulation of the ear, eye stimulation, mechanical stirrer, etc.). The device also analyzes the respiratory activity to evaluate the effectiveness of the stimulation so that the patient or the physician can change the setting of the generator as desired with different doses of the stimuli.

US 2008/0154330 A1 describes an electrical stimulation system of the diaphragm to stabilize breathing. Therapy is triggered when a respiratory instability is detected and stopped when a predetermined number of stable cycles were detected. No indication is given about a possible optimization of the therapy based on a respiration stability analysis. Moreover, this therapy by stimulation of the diaphragm is not applicable to obstructive apnea or hypopnea.

Finally, WO 2009/154458 A2 teaches a system which detects apnea and in turn causes an inspiration reflex by stimulation in the ear region. Various apnea detection methods are illustrated. The stimulation may be electrical or mechanical. The stimulation strategy is minimal; it is to apply pulse trains as long as the disorder is present. However, it is indicated that the stimulation parameters may vary, without, proposed variation rules. A random variation of the parameters is also cited to avoid habituation. However, this document is very vague on the stimulation parameters. It only very generally discloses:

Mechanical, electrical or acoustic stimulation;
A stimulation frequency between 1 and 500 Hz; and
A duration of stimulation and a waiting time between two stimuli varying between 0.5 and 10 s.

The stimulation will be more or less effective depending on the chosen values, for example the brainstem elements have a sensitivity which varies greatly with the frequency range. Furthermore, by randomly varying the stimulation energy, the risk is a less effective therapy (if energy is too low) or waking the patient (if energy is too high). Finally, in this document, the therapy stops as soon as there is respiratory recovery, such as from the detection of an inspiratory reflex that is expected to be triggered.

Thus the prior art provides very little teaching on a precise method for the stimulation delivery. However, a poorly adjusted or random stimulation can cause:

Inefficiency, if the stimulation is not appropriate and adapted to the response that is desired to be caused by the stimulation;

Short or medium term addiction resulting in an ineffective therapy, if the therapy is issued too often or misused;

Finally, a patient arousal and therefore sleep disintegration, which is to be avoided by treating the apnea.

SUMMARY

A first aspect of the present invention relates to a fine adjustment of stimulation parameters which can have a significant impact on the quality and effectiveness of therapy.

A second aspect of the invention relates to a fine temporal control of the stimulation period, especially the stopping time, which can have a significant impact on the quality and effectiveness of therapy.

More specifically, according to certain aspects, disclosed is a device for treating a respiratory disorder in a patient by kinesthetic stimulation, including:

A processor configured to produce kinesthetic stimulation control signals in response to the detection of a respiratory disorder; and At least one kinesthetic effector adapted to be applied to a patient's external skin site, and including a vibrating electromechanical transducer capable of receiving control signals and outputting a kinesthetic stimulation energy determined by the control signals.

According to the aforementioned first aspect, the processor is further configured to provide automatic determination of the therapy, including dynamically selecting, based on a type of expected or detected disorder, a strategy of stimulation from a set of stored simulation strategies.

According to various embodiments:

The stimulation strategies may include at least one strategy by stimulation pulse of a first type and at least one stimulation strategy by stimulation pulse of a second type, the pulses of the second type having a pulse duration greater than the first type and/or pulses of the second type being spaced apart by a time interval greater than the pulses of the first type;

The pulses of the first type may have a pulse duration between 2 and 3 seconds and are spaced apart by a time interval between 2 and 3 seconds, and the pulses of the second type have a pulse duration greater than that of the pulses of the first type and are spaced apart by a time interval greater than the pulses of the first type;

The automatic therapy determination may include capping the value of the stimulation energy to a maximum value;

The automatic therapy determination may include selecting, depending on the type of expected or detected disorder, either a high energy stimulation strategy and early therapy, or a low energy stimulation strategy and later therapy;

The automatic therapy determination may include incrementally raising the energy level from the initial value, as long as an existing respiratory disorder does not disappear;

The automatic therapy determination may include comparing each incremented energy value to a maximum value;

The automatic therapy determination may include forcing the energy level to a value greater than the maximum permissible value, upon detection of a severe episode of the respiratory disorder.

The second aspect cited above utilizes a device including:

A processor configured to produce kinesthetic stimulation control signals in response to the detection of a respiratory disorder; and At least one kinesthetic effector adapted to be applied to a patient's external skin site, and include a vibrating electromechanical transducer capable of receiving control signals and outputting a kinesthetic stimulation energy determined by said control signals; wherein The processor is further configured to determine the effectiveness of a stimulation, and is able to detect the disappearance of the respiratory disorder.

In a manner characteristic of the second aspect, the processor is further configured to extend the stimulation control during a determined stabilization period following the disappearance of the respiratory disorder.

According to various embodiments:

Extending the stimulation control may occur after the disappearance of the disorder pulses with the same duration and same spacing as those that caused the disappearance of the disorder;

The processor may be further configured to determine the duration of extension of the stimulation control from a number of consecutive breathing cycles following the resumption of breathing at the disappearance of the disorder;

The processor may be further configured to monitor the occurrence of a new episode of respiratory disorder for a given duration after the end of a disorder episode;

The processor may be further configured to change the extension duration of the stimulation control, depending on whether or not of a new episode of respiratory disorder during said given stabilization duration occurs;

The processor may be further configured to dynamically adjust the duration of extension of the stimulation control by a learning function of possible recurrences observed over time;

The processor may be further configured to adapt to limit the delivery of kinesthetic stimulation energy to a predetermined number of successively delivered stimulation pulses;

The predetermined number of pulses may assume two different values, depending on the type of respiratory disorder.

BRIEF DESCRIPTION OF THE DRAWINGS

Further features, characteristics and advantages of the present invention will become apparent to a person of ordinary skill in the art from the following detailed description of preferred embodiments of the present invention, made with reference to the drawings annexed, in which like reference characters refer to like elements and in which.

DETAILED DESCRIPTION

Figure 1:
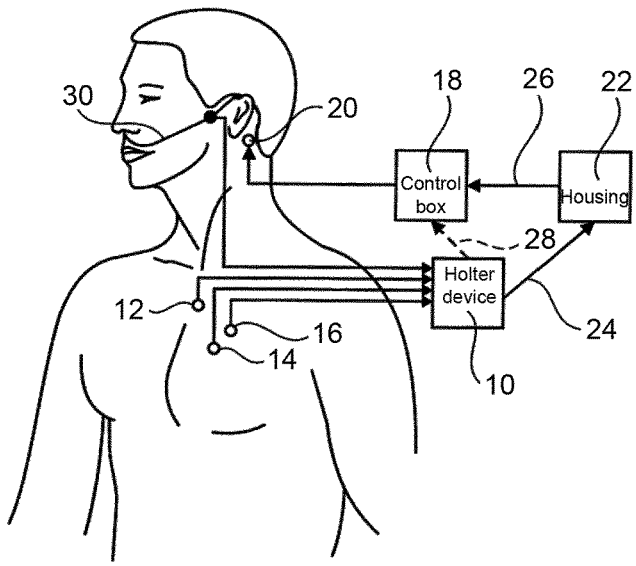
FIG. 1 schematically illustrates a system, according to an embodiment the invention, placed on a patient.

FIG. 1 schematically illustrates the main components of a system used for the implementation of the present disclosure.

The system includes a Holter device 10 connected to various sensors or electrodes 12, 14, 16, for measuring physiological signals such as heart rate, respiration, oxygen saturation, pulse wave, phonocardiogram, etc. The present disclosure focuses mainly on the respiratory amplitude or respiratory pressure, which are simple parameters to obtain. However this measure is not intended to be restrictive and the disclosed system and methods can be implemented from other physiological signals collected from the patient as well.

The system further comprises a kinesthetic stimulation device, with a generator housing 18 producing pulses for control of a stimulation kinesthetic effector 20, consisting, for example, of a vibrator disposed in a sensitive region of the skin, typically (in adults) in the mastoid bone region near the ear. Vibrotactile stimulation applied to the skin by the effector 20 is detected by the sensory receptors or mechanoreceptors of the body, and this information is transmitted through sensory nerves to the autonomous central nervous system.

The effector 20 is, for example, a transducer such as C10-100 of Precision Microdrives or C2 Tactor of Engineering Acoustics. The transducer is of a few grams which can emit vibrations due to an integrated vibrator excited by pulse trains of variable amplitude and length, typically at a frequency of 250 Hz which is the nominal resonance frequency of this particular effector, and which is also the frequency at which the mechanoreceptors of the skin are the most sensitive. However, other types of effector can be used effectively.

The control box 18 is controlled by a microcontroller and is configured to adjust the intensity (i.e., the energy) of kinesthetic stimulation by controlled variation of the amplitude, the number, the duration, and/or the frequency of the stimulation pulse trains forming the signal applied to the effector 20.

The system also includes a housing 22 coupled to the Holter device 10 and to the control box 18 by a respective wire or wireless connection 24, 26, to receive data from the Holter device 10, process such data, and in response produce information of kinesthetic stimulation control to be transmitted to the control box 18. Alternatively, data processing and control of the control box 18 can be operated within the Holter device 10 and transmitted directly by a link 28 to the housing 18.

Finally, the system is configured to measure the respiratory rate via, for example, a nasal pressure cannula 30 (and/or an oral cannula) or other type of sensor such as a thermistor or a mechanical sensor of the abdomen and/or the thoracic cavity volume changes (e.g., by a belt equipped with sensors sensitive to stretching, etc.). The nasal pressure cannula 30 delivers a ventilatory signal to the Holter device 10 which is continuously analyzed in order to detect in real time the occurrence of an apnea or of a hypopnea.

The system operates as follows: when apnea is detected by the Holter device 10, the control box 18 triggers a kinesthetic stimulus to trigger a response of the autonomic nervous system so that, in response, the autonomic nervous system causes a change in respiration and therefore triggers a respiratory reflex that stops apnea.

According to exemplary embodiments, the system is able to trigger different stimulation modes, depending on the type of respiratory disorder.

In this regard, the stimulation mechanism of the events to be treated has been adapted in order to optimize the effectiveness of the stimulation. Specifically, hypopneas and apneas are divided into two main groups: central apnea and obstructive apneas. Thus, although both types of events can generally be stopped by a kinesthetic stimulation using the system described above, the operating mechanism of this stimulation should preferably be differentiated to be effective.

First the case of central apnea is described. The operating mechanism of the apneas/hypopneas in the system according to the disclosure is based on stimulation of the autonomic nervous system or sympathovagal reflex. This type of response is easily obtained non-invasively by stimulating mechanoreceptors in the skin.

Studies show that during sleep, the autonomic nervous system remains responsive to external sensory stimuli and causes a physiological response. Therefore, the application of stimulation on the skin during sleep triggers a sympathovagal response that acts not only on the heart rate and the blood pressure but also on the breathing characteristics.

Figure 2:
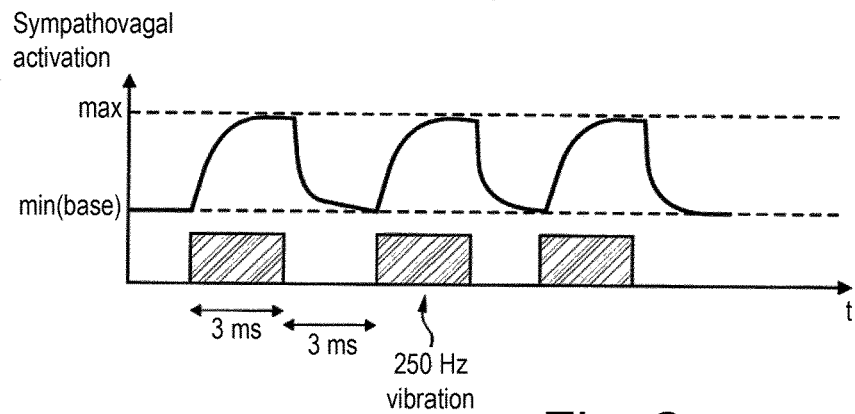
FIGS. 2 and 3 are timing diagrams illustrating stimulation pulses applied to a patient, modeling the resulting changes in sympathovagal balance, respectively, for two different pulse durations.

Thus the timing diagram of FIG. 2 illustrates an effective stimulation of the sympathovagal balance. Stimulation is performed by pulse bursts (hereinafter "pulses") during which a mechanical vibration is enabled at the frequency of 250 Hz, a frequency at which the mechanoreceptors of the skin are more sensitive and is therefore optimal for kinesthetic stimulation.

The duration of such a pulse corresponds to the achievement of the maximum level of stimulation of the sympathovagal balance. Thus, it is desirable to trigger reflexes in an effective method dependent on this stimulation, including increased respiration. In an exemplary method, the duration of the pulses is between about 2 and 3 s.

Once the maximum level is reached, stimulation is stopped to allow the sympathovagal system to recover as quickly as possible. When sympathovagal balance has returned to its basis minimal level, stimulation can be restarted without loss of efficiency and without the risk of habituation to stimulation. In an exemplary method, the pulse interval is also between 2 and 3 s.

Figure 3:
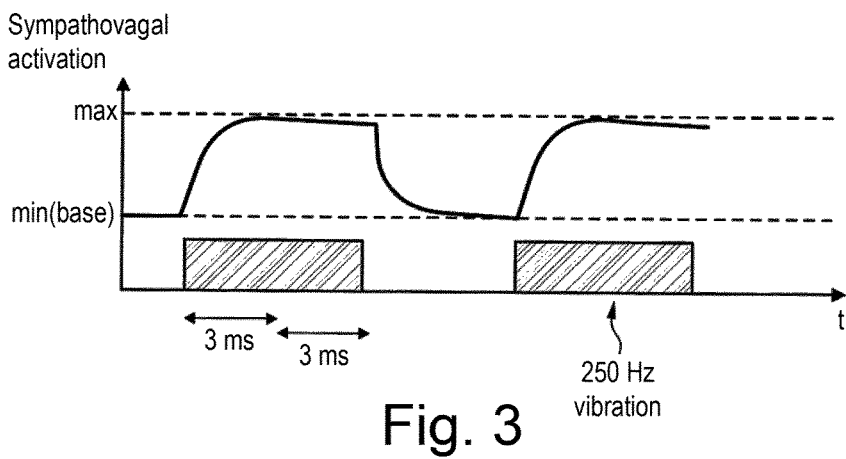

FIG. 3 illustrates a situation where the stimulation pulses are too long. The pulses continue while sympathovagal activation has reached a plateau. The extension of the pulses does not increase the efficiency of stimulation for the reflexes that were maximally engaged at the beginning of the plateau. In contrast, it slows down the recovery of the system that, is saturated. Also, if the first stimulus did not have the desired effect, the extension of the pulse delays the issuance of the next pulse, and thus delays the possibility of halting the respiratory disorder.

Conversely, with too short of stimulation pulses, the risk is not effectively stimulating the sympathovagal balance and therefore not causing the expected reflexes (typically an increase in cardiac frequency, in voltage or in breathing).

In summary, the important parameters of a kinesthetic stimulation for central apneas/hypopneas are:

A mechanical vibration frequency of 250 Hz;
A pulse duration of about 2 to 3 seconds; and
A pulse interval (recovery time) of about 2 to 3 seconds.

These parameters are used to optimize the sympathovagal response while avoiding habituation and allowing the therapy to repeat as early as possible in case of ineffective therapy.

The case of an obstructive apnea/hypopnea is now considered. The objective of kinesthetic stimulation in obstructive sleep apnea is to stimulate the nerves of the muscles controlling the breathing, including the hypoglossal nerve.

The mechanism explained above may be effective in some episodes or some people, since the triggering of the sympathovagal response will also stimulate nerve functions and therefore the hypoglossal nerve, but this mechanism might not be enough.

It is desirable, unlike with central apnea, to apply a direct stimulation of 10 seconds or more to stimulate a maximum number of nerve fibers. The frequency of stimulation vibrations preferably remains the same, around 250 Hz. The purpose is no longer to trigger a reflex but to recruit a maximum number of nerve fibers near the stimulation point.

Figure 4:
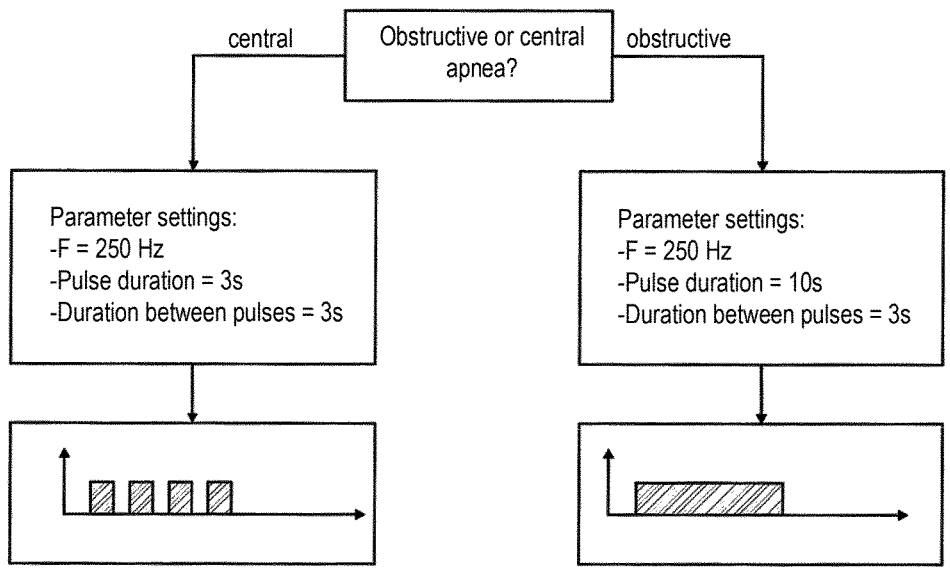
FIG. 4 schematically illustrates a method of selecting between two sets of stimulation parameters based on the type of observed disorder.

Between these two therapy possibilities, the selection of the pacing mode is done automatically by the device, in response to differentiation in real time of the central/obstructive episodes, and/or according to the efficacy of one therapy or the other. FIG. 4 schematically illustrates the differentiation and selection between the two respective stimulation strategies adapted in this example to the two types of apnea.

Furthermore, the stimulation system of the disclosure is suitable for treating the clinical events in a differentiated method.

For example, apnea is a serious episode that may lead to rapid desaturation. Moreover, this disorder, characterized by an absence of respiratory flow, is easy to diagnose with good sensitivity and specificity. Finally, it is important to stimulate an apnea episode as fast as possible because it will be reduced more easily if it is taken care of quickly.

In contrast, a hypopnea is a more common clinical phenomenon, but less severe immediately. The detection of hypopnea is more delicate and good sensitivity is usually accompanied by a poor specificity. This poor specificity may create a significant number of false positive stimuli, and these over-stimulations can lead to unexpected awakenings.

To address these issues, the system according to the present disclosure is capable of applying a therapy which varies according to the detected disorder, preferably in respect to the following aspects:

Early treatment: apnea will be treated, for example, within 5 to 10 seconds after the detection, in order to act at the earliest; however, hypopnea will be processed, for example, in a period of 10 to 15 s after detection, which allows the system to avoid applying a stimulation on false positives or on light and spontaneously reduced hypopnea;

Therapy energy: upon detection of an apnea, one must be sure to apply an effective, thus potentially higher energy; however, for a hypopnea, the system can start stimulation with lower energy, so with less risk of waking the patient, even if this energy increases if the disorder continues.

While a differentiation between therapies for apnea and hypopnea is proposed in the foregoing, it will be understood that this principle can be applied to other respiratory disorders, of differentiable respective types. One could, for example, differentiate the therapy depending on the nature of the apnea (central or obstructive), the nature of hypopnea (central or obstructive), the level of the desaturation accompanying the episode, etc.

Figure 5:
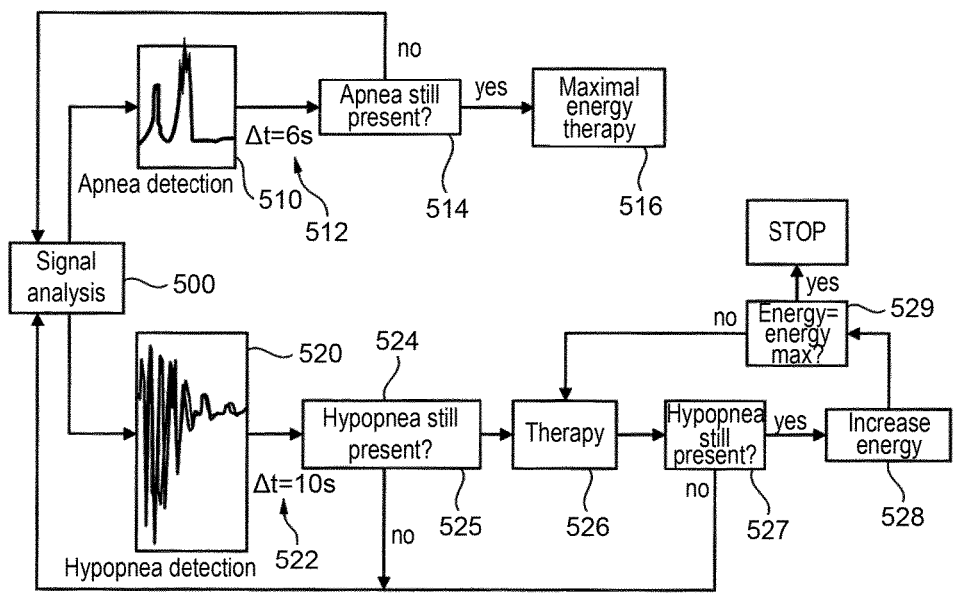
FIG. 5 is a more detailed flow chart of the various steps of the selection and a stimulation application method with different parameters depending on the type of disorder.

FIG. 5 schematically illustrates the different actions implemented by a processing system of the disclosure. In step 500, the system analyzes the signals provided by the sensors 12, 14, 16, 30 (or only one of them) for performing a differentiation between apnea (block 510) and hypopnea (block 520). If an apnea is detected, the system applies a time delay $\Delta t$, for example, 6 s (step 512) prior to determining (step 514) if the apnea is still present. If so, the therapy is applied with the nominal energy adapted for this type of disorder—a higher energy than for a hypopnea (step 516). If not, the method returns to step 500 of signal monitoring.

If a hypopnea is detected, the system applies a time delay $\Delta t$, for example 10 s (step 522), and then determines (step 524) if the hypopnea phenomenon is still present. If so, the system determines a minimum level of stimulation energy (step 525) and applies a pacing therapy (step 526) with that energy level. Then the system again determines if the hypopnea is present (step 527). If so, the level of stimulation energy is increased by a given increment (step 528) and the therapy (step 526) is implemented with this new energy. Then it is checked again if the hypopnea is present (step 527).

The test of maximum energy (step 529), implemented after each energy increment, limits the energy level to a ceiling (typically below the energy level that can cause a patient's waking), and discontinues the therapy when this energy level is reached. In all cases, the stimulation strategy itself (including the pulse width and the spacing between pulses) is determined by the system dynamically, depending on the type of disorder (central or obstructive).

A second aspect of the system of the disclosure relates to when the stimulation is stopped after a recovery of respiration.

Figure 6:
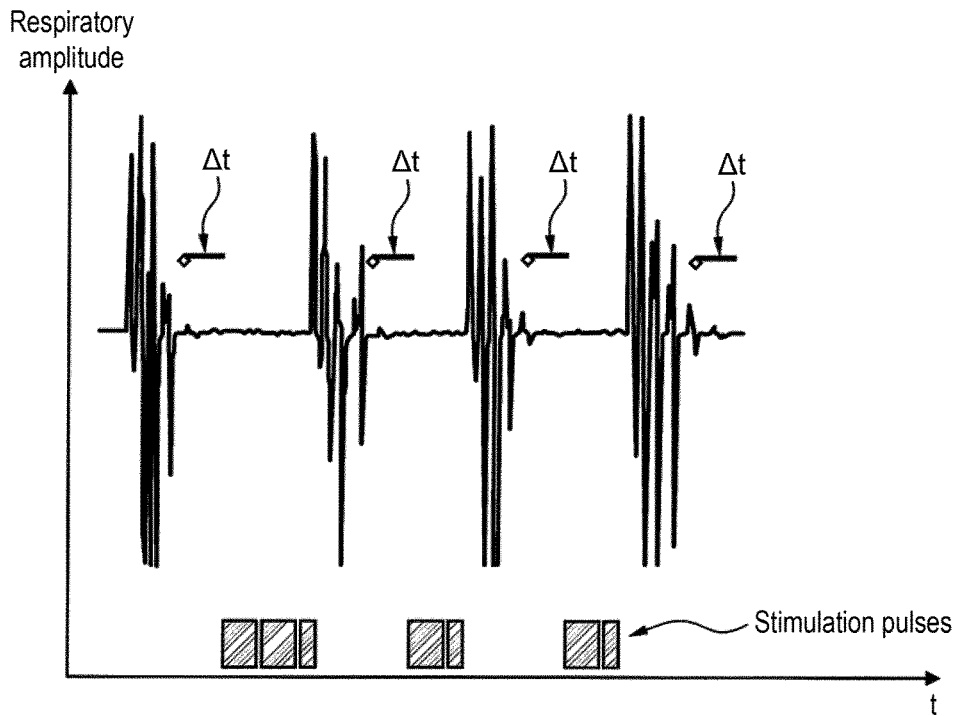
FIG. 6 is a timing diagram illustrating the stopping of the stimulation after the disappearance of the disorder, according to the prior art.

In the prior art, it is recommended to stop the stimulation when the respiratory signal is present. However, early cessation of stimulation in certain conditions could cause early recurrences of respiratory disorders, as shown in FIG. 6. FIG. 6 illustrates the case in which kinesthetic stimulation pulses are applied by the processing module after a specified period $\Delta t$, with appropriate energy. As soon as the respiratory recovery is observed (recovery of the amplitude of the signal detecting breathing, as illustrated), the therapy stops at the risk, as shown in this example, of an early return of respiratory disorder.

Figure 7:
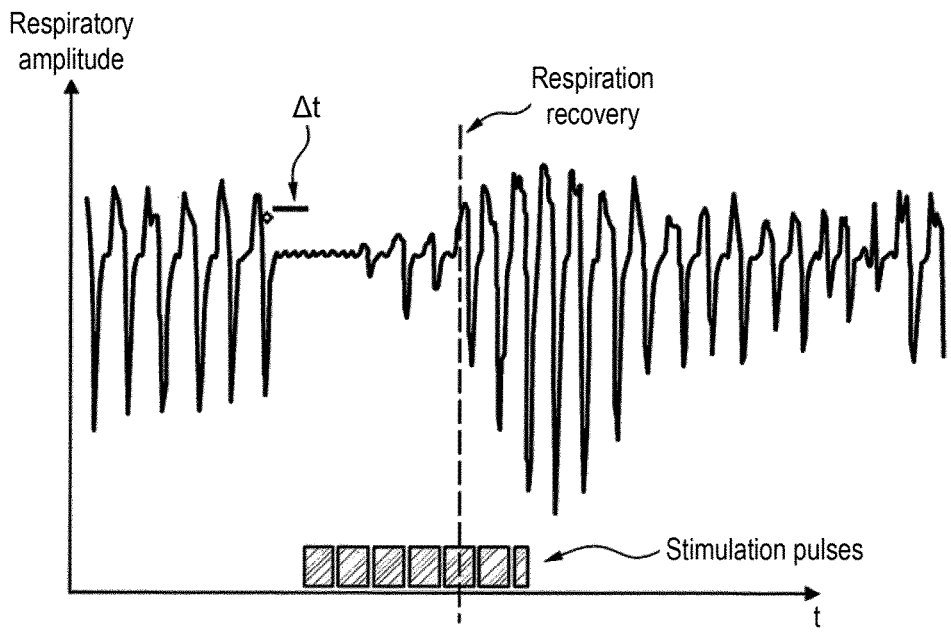
FIG. 7 is a timing diagram illustrating the stopping of the stimulation after the disappearance of the disorder, according to one aspect of the invention.

FIG. 7 shows the system implemented according to the second aspect of the disclosure, where the kinesthetic stimulation pulses are extended beyond the time where the signal analysis determines the resumption of the ventilation. The extension allows the ventilation to sustainably recover, while minimizing the risk of early recurrence.

The example illustrated in FIGS. 6 and 7 is that of obstructive apneas or hypopneas.

In some cases, it may also be important to impose a limit on the number of delivered pulses. Beyond a certain number, it is likely that the lack of response is due to ineffective therapy. Therefore, it may be useless to continue to deliver pulses unnecessarily, which may awaken the patient.

The limit may be different depending on the delivered therapy. In the case of a short pulse therapy which therefore consists of triggering a response from the sympathovagal balance, the produced reflex is an "all-or-nothing" type. If the first few delivered pulses (e.g., the first three) with appropriate amplitude have failed to trigger the reflex, the therapy is not effective and it is not useful to stimulate more at the risk of waking the patient. In contrast, in the case of therapy consisting of long pulses to recruit the nerve fibers, the maximum of number of pulses is greater, typically between 10 and 15 pulses, to ensure the maximum of nerve fibers are recruited.

The additional duration, or settling time, which elapses between the detection of the respiratory recovery and the end of the stimulation may be fixed or programmable, or dynamically adjusted based on various criteria. Thus, learning can be advantageously provided to best determine this duration, expressed for example by the number of breaths to be observed prior to therapy discontinuation and/or depending on any recurrence over time.

In the example of FIG. 7, the system applies pulses having the same duration and the same interval as those that caused cessation of the disorder after the resumption of respiration. The pulse are applied for a period corresponding to three respiratory cycles of amplitude greater than a certain threshold.

Figure 8:
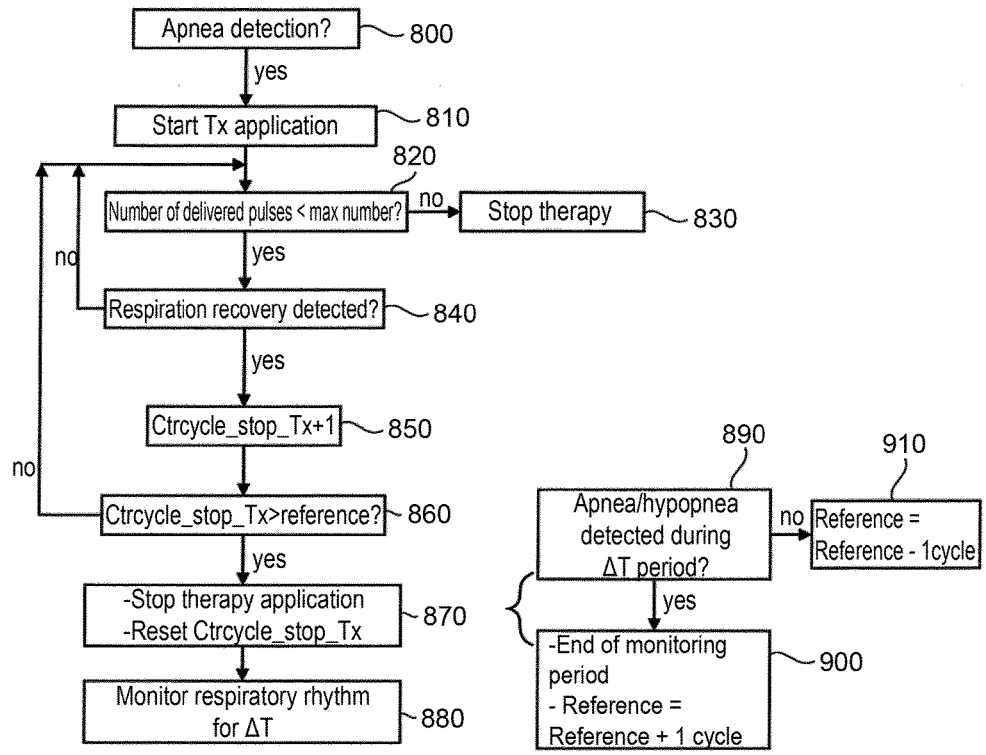
FIG. 8 is a detailed flowchart of a method of adjusting the stopping time of stimulation according to the above aspect.

FIG. 8 shows the steps implemented by the system to perform this function. Step 800 is the detection of a respiratory disorder. When such a disorder is detected, a Tx stimulation therapy is selected depending on the type of disorder (typically apnea/hypopnea, and central/obstructive) and applied in step 810.

During therapy application, the system checks in step 820 if the number of pulses delivered is less than the maximum number allowed for the type of ongoing therapy, for example three pulses for a short pulse therapy (response of the sympathovagal system) and ten pulses for a long pulse therapy (recruitment of fibers). If the maximum number of pulses is reached, the therapy is stopped in step 820 even if the ventilatory recovery has not taken place, as it is assumed that the therapy is not effective and should no longer delivering ineffective stimulation, to avoid waking the patient.

Still during application of the Tx therapy, the system detects in step 840 if the respiratory activity resumes. If so, steps 850 and 860 respectively perform a count of the number of breathing cycles following the resumption of breathing (Ctrcycle_stop_Tx parameter) and a comparison of the count with a reference value which indicates the number of respiratory cycles, after recovery, for which stimulation should continue. When the reference value is reached, the system stops the application of pulses and resets the value of the Ctrcycle_stop_Tx count (step 870).

Next, at step 880, the respiratory rate is monitored for a period ΔT and a test is performed at step 890 to determine if an apnea or a hypopnea phenomenon occurs during this period. If so, the reference value is incremented by a given value, for example by one unit (step 900), so that on a subsequent pacing, the stimulation phase after resumption of breathing continues for a longer duration.

If not, the reference value is reduced by the same given value, for example by one unit (step 910), so that on a subsequent pacing, the stimulation phase after resumption of breathing continues for a shorter duration. The reduction of the reference value avoids a systematic drift of the therapy extension duration setting in case of frequent resumptions of a disorder in the post-therapy monitoring.

Figure 9:
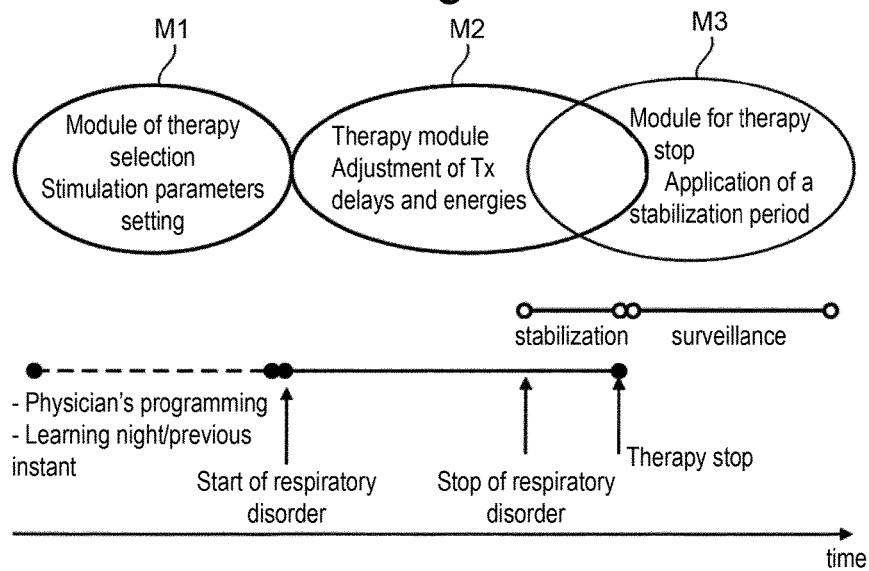
FIG. 9 illustrates the arrangement of various control functions of the stimulation in a time diagram, according to the teachings of the disclosure.

FIG. 9 illustrates in a time diagram the arrangement and interaction of the various features described hereinabove, namely:

The function of selecting a particular stimulation therapy adapted to the type of expected or detected respiratory disorder;

The function of dynamically adjusting the energy and temporal parameters of applied stimulation pulses; and The function of determining a controlled stimulation stop after the resumption of respiratory activity.

These features are implemented by three specific hardware or software modules respectively M1, M2, and M3 implemented in the housing 22, it being noted that the module M2 for adjustment of the stimulation parameters and the module M3 for determination of the stop are active in parallel during the stabilization period.

What is claimed is:

1. A system for treating a respiratory disorder in a patient by stimulation, including:
   a processor configured to generate stimulation control signals in response to detection of a respiratory disorder; and
   at least one effector adapted to receive the stimulation control signals and to deliver a stimulation energy responsive to the stimulation control signals;
   wherein the processor is further configured to:
      determine an effectiveness of the stimulation energy by detecting a cessation of a respiratory disorder episode;
      detect a resumption of breathing after the cessation of the respiratory disorder episode;
      extend the stimulation control signals during a determined stabilization period following the cessation of the respiratory disorder episode; and
      determine an extension length of time for the stimulation control signals based on a number of breathing cycles following the resumption of breathing.

2. The system of claim 1, wherein the extended stimulation control signals are applied after the cessation of the respiratory disorder episode and include pulses having a pulse duration and an interval between pulses that are consistent with pulses that caused the cessation of the respiratory disorder episode.

3. The system of claim 1, wherein the processor is further configured to monitor the patient for an occurrence of a new episode of the respiratory disorder for a given duration after the cessation of the respiratory disorder episode.

4. The system of claim 3, wherein the processor is further configured to change an extension length of time of the stimulation control signals, depending on the occurrence or an absence of the new episode of the respiratory disorder, during the determined stabilization period.

5. The system of claim 1, wherein the processor is further configured to dynamically adjust a duration of the extended stimulation control signals by a learning function analyzing any recurrences of episodes of the respiratory disorder observed over time.

6. The system of claim 1, wherein the processor is further configured to limit the delivery of stimulation energy to a predetermined number of successive stimulation pulses.

7. The system of claim 6, wherein the predetermined number of successive stimulation pulses is one of two different values, selected by the processor depending on a type of the respiratory disorder.

8. The system of claim 1, wherein the stimulation is kinesthetic stimulation.

9. The system of claim 8, wherein the at least one effector comprises at least one kinesthetic effector adapted to be applied to a patient's external skin site and comprising a vibrating electromechanical transducer.

10. A system for treating a respiratory disorder in a patient by kinesthetic stimulation, including:
- a processor configured to generate kinesthetic stimulation control signals in response to detection of a respiratory disorder; and
- at least one kinesthetic effector adapted to be applied to a patient's external skin site, and comprising a vibrating electromechanical transducer adapted to receive control signals and to deliver a kinesthetic stimulation energy responsive to said control signals;
- wherein the processor is further configured to:
  - determine an effectiveness of the kinesthetic stimulation energy by detecting a cessation of a respiratory disorder episode;
  - detect a resumption of breathing after the cessation of the respiratory disorder episode;
  - extend the stimulation control signals during a determined stabilization period following the cessation of the respiratory disorder episode; and
  - determine an extension length of time for the stimulation control signals based on a number of breathing cycles following the resumption of breathing.

\* \* \* \* \*